United States Patent [19]
Sommers et al.

[11] Patent Number: 6,165,625
[45] Date of Patent: Dec. 26, 2000

[54] METHOD OF MAKING HIGH INTENSITY LIGHT RESISTANT INSTRUMENT PADS

[75] Inventors: Jay R. Sommers, Marietta; Richard C. Dowdy, Duluth; Hilary Walker, Marietta; D. Mark Foreste, Roswell, all of Ga.

[73] Assignee: Kimberly-Clark Worldwide, Inc., Neenah, Wis.

[21] Appl. No.: 08/769,933

[22] Filed: Dec. 19, 1996

[51] Int. Cl.$^7$ .............................. B32B 27/08; A61F 5/37
[52] U.S. Cl. .................. 428/515; 422/516; 422/518; 422/520; 422/336; 128/846; 128/849; 128/857
[58] Field of Search ..................... 428/515, 516, 428/518, 520, 336; 128/846, 849, 857

[56] References Cited

U.S. PATENT DOCUMENTS

| | | | |
|---|---|---|---|
| 3,263,680 | 8/1966 | Morgan | 128/132 |
| 3,668,050 | 6/1972 | Donnelly | 101/39 |
| 3,669,106 | 6/1972 | Schrading et al. | 128/132 D |
| 3,738,359 | 6/1973 | Lindquist et al. | 128/132 R |
| 3,881,474 | 5/1975 | Krzewinski | 128/132 D |
| 3,902,484 | 9/1975 | Winters | 128/132 D |
| 3,974,308 | 8/1976 | Winters | 427/244 |
| 4,520,814 | 6/1985 | Weeks | 128/303.1 |
| 4,601,286 | 7/1986 | Kaufman | 128/132 D |
| 4,611,588 | 9/1986 | Laptewicz, Jr. et al. | 128/132 R |
| 4,616,641 | 10/1986 | Teeple | 128/132 R |
| 4,735,623 | 4/1988 | Hatzenbuhler et al. | 604/369 |
| 4,901,738 | 2/1990 | Brink et al. | 128/849 |
| 5,033,479 | 7/1991 | Tanny | 128/849 |
| 5,036,866 | 8/1991 | Eldridge, Jr. et al. | 128/849 |
| 5,151,095 | 9/1992 | Teeple, Jr. | 606/2 |
| 5,190,810 | 3/1993 | Kirschbaum et al. | 422/246 |
| 5,212,387 | 5/1993 | Swan | 250/515.1 |
| 5,225,236 | 7/1993 | Keusch et al. | 428/77 |
| 5,381,802 | 1/1995 | Schwartzenfeld | 128/857 |
| 5,509,271 | 4/1996 | Taub | 156/306.3 |

FOREIGN PATENT DOCUMENTS

| | | |
|---|---|---|
| 64463/80 | 8/1994 | Australia . |
| 0 328 225 | 8/1989 | European Pat. Off. . |
| 0 635 245 A1 | 10/1989 | European Pat. Off. . |
| 296 17 010 | 1/1997 | Germany . |
| 1388749 | 3/1975 | United Kingdom . |
| 2073009 | 10/1981 | United Kingdom . |
| 95/13605 | 5/1995 | WIPO . |

OTHER PUBLICATIONS

"Laparoscopy Light Cable Ignites Operation Room Firm", *Biomedical Safety & Standards*, vol. 24, No. 21, Dec. 1, 1994, pp 162–163.

"OR Fires: Preventing Them and Putting Them Out", *Health Devices*, vol. 15, No. 5, May 1986, p 132.

"Fire Safety in the Operating Room", *Today's O.R. Nurse*, vol. 14, No. 3, Mar. 1992, pp 8–10.

"Surgical Drapes", *Health Devices*, vol. 15, No. 5, May 1986, pp 111–140.

Copy of Search Report for PCT/US97/22795 dated Apr. 24, 1998.

Abstract for DE 296 17 010 U1., 1998.

Abstract for WO 95/13605., 1998.

"Fiberoptic Illumination Systems Can Serve as a Source of Smoldering Fires", M.A. Eggan and J.G. Brock–Utne, *Journal of Clinical Monitoring*, v. 10, No. 4, Jul. 1994, pp. 244–246.

"OR Fires Caused by Fiberoptic Illumination Systems", *Health Devices*, v. 11, No. 11, Mar. 1982, pp. 148–149.

*Primary Examiner*—Leszek Kiliman
*Attorney, Agent, or Firm*—Nancy M. Klembus; Jones & Askew Attys.

[57] ABSTRACT

Improved instrument pad surgical drape for use during surgical procedures is disclosed which is resistant to melting caused by high intensity light generated from sources such as fiberoptic illumination systems. The instrument pad and drape comprise an infrared energy reflective film/foam laminate that may also have a high coefficient of friction which is useful for retaining surgical instruments in place and preventing them from slipping off the pad during a surgical procedure.

15 Claims, 3 Drawing Sheets

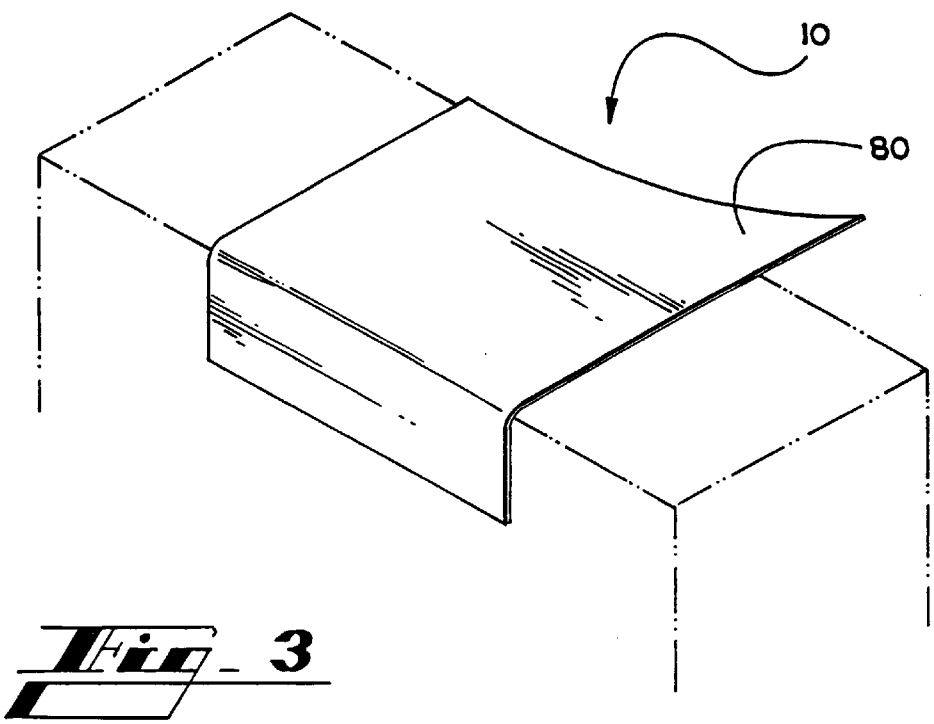
Fig_3
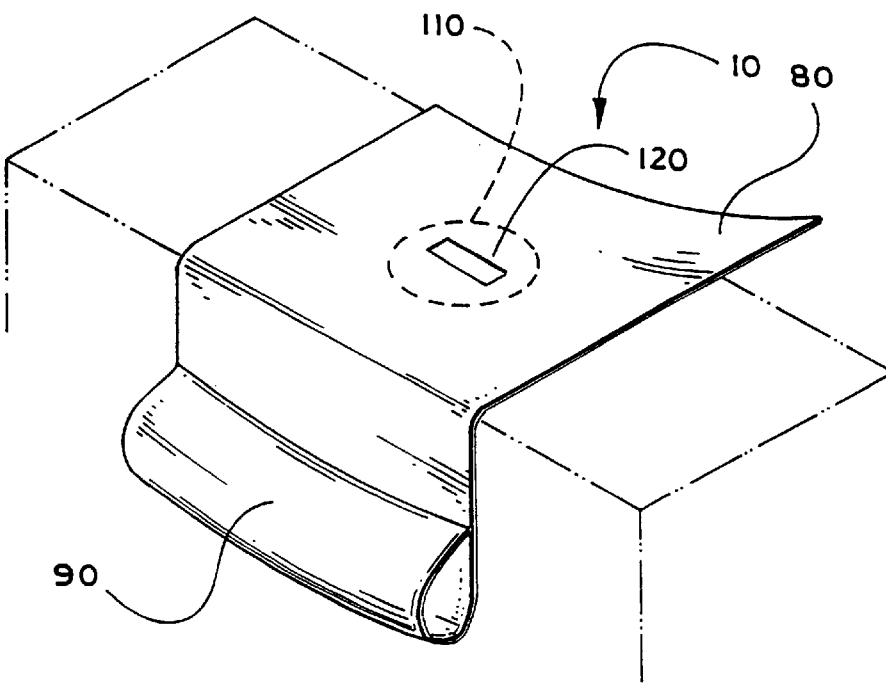
Fig_4

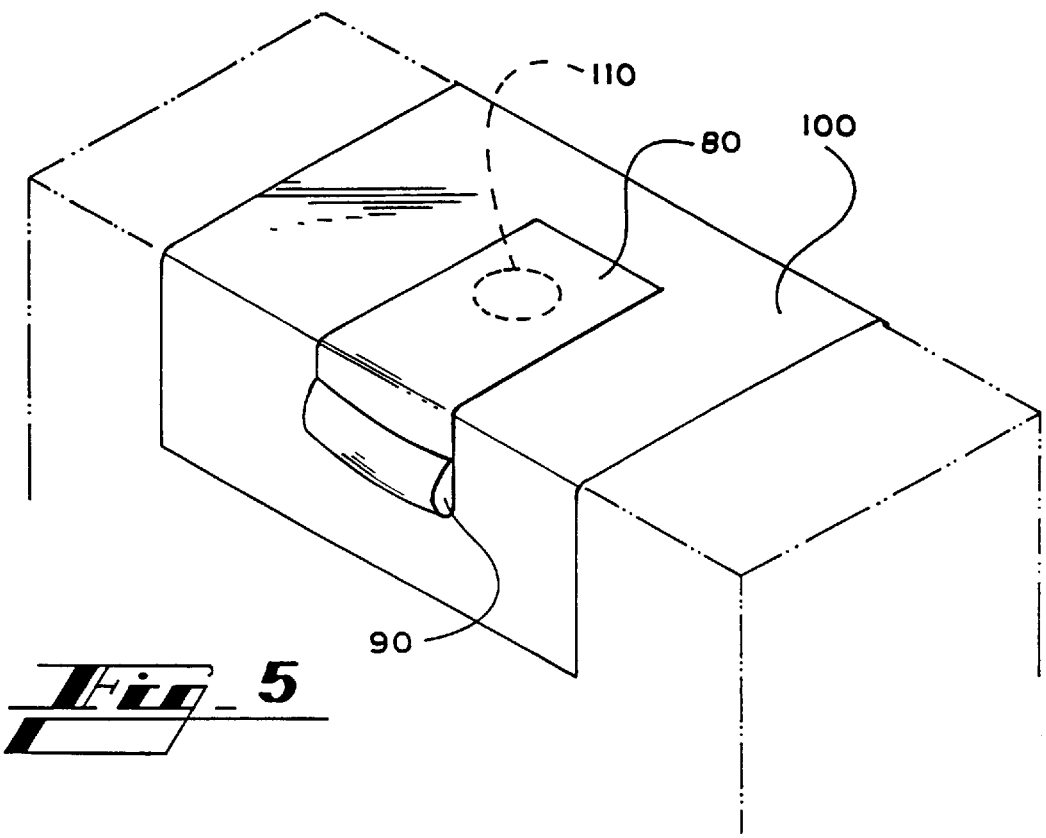
Fig_5
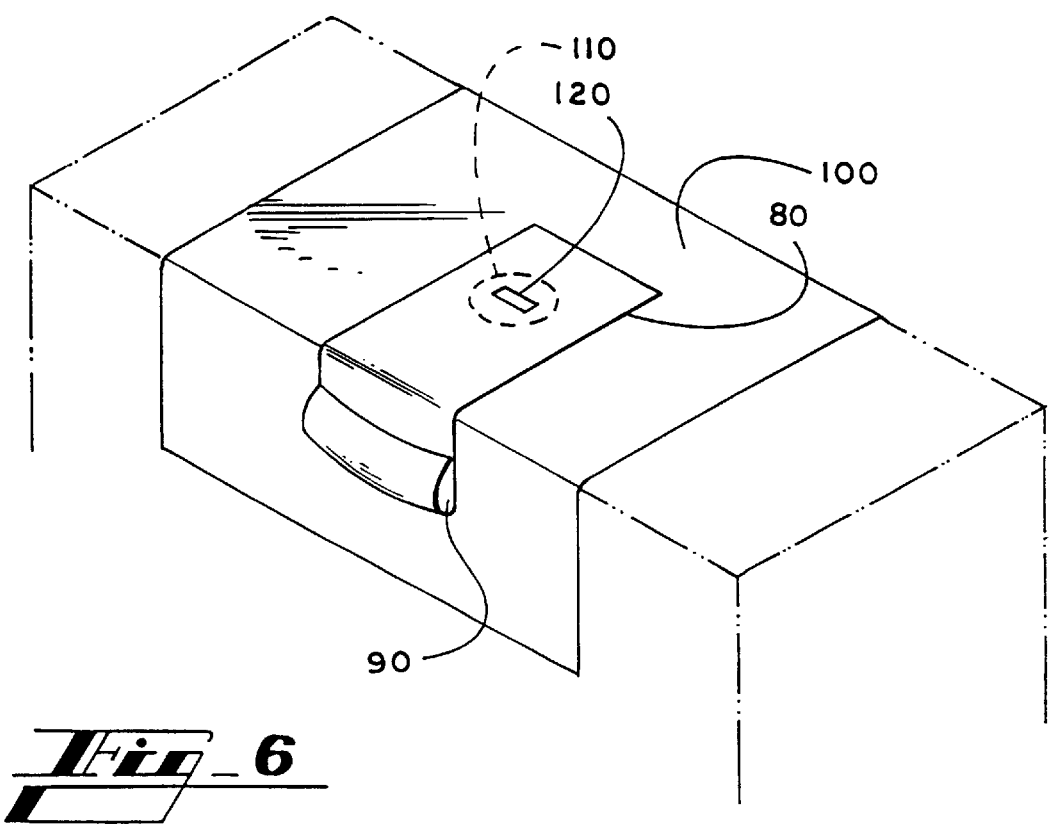
Fig_6

METHOD OF MAKING HIGH INTENSITY LIGHT RESISTANT INSTRUMENT PADS

FIELD OF THE INVENTION

The present invention relates to a composition of sheet material comprising a film/foam laminate as a supporting surface for articles, particularly surgical instruments. Most significantly during surgical operating conditions, the white or transparent materials resist melting when exposed to light from high intensity light sources such as xenon lamps that are used in fiberoptic illumination systems.

BACKGROUND OF THE INVENTION

During delicate and intricate surgical procedures it is imperative that surgeons and other medical staff be able to work in very well lighted conditions. Many times surgery involves incisions that must traverse several layers of body tissue in order for the surgeon to reach his target. Consequently the incision often results in an opening that is difficult to see through because of blood and other body fluids and components such as fatty tissue. Since most surgical procedures allow very little room for error, superior lighting conditions are absolutely necessary during surgery so that the surgeon and medical assistants may clearly observe the patient, as well as the surgical opening, the instruments and whatever monitoring devices that are being used.

In the past a wide variety of lighting has been employed in the operating room. Fiberoptic illumination systems however have emerged as a preferred method of lighting because they permit a highly enhanced degree of visibility and are therefore frequently the lighting systems selected for use in many operating rooms. Recently there has been an overall increase in the use of fiberoptic illumination systems both in operating rooms and in out-patient centers.

Most fiberoptic systems consist of a light source or projector, and a light transmitting cable. These systems are often used with many types of endoscopes (e.g. laparoscopes, cystoscopes, etc.), surgical headlamp sets, fiberoptic retractors, and suction instruments.

Many of the light sources used with fiberoptic illumination systems employ a 300 watt xenon lamp, primarily because these lamps have been available for many years, and also because they generate the maximum light intensity. Because of their brightness, many physicians prefer them to the newer, lower intensity systems (e.g. 150 watt xenon, halogen or metal halide lamps). Xenon lamps emit many energy bands in the near infrared region, some of which are fairly intense. (*Handbook of Chemistry and Physics*, 41 st. ed., Chemical rubber Publishing Company: Ohio, 2890–2891, 1960.) According to some vendor's spectral distribution charts, xenon emission is primarily reported to be in the 350–700 nm wavelength; however such spectrums are usually arrived at using shielded cables which absorb much infrared radiation. It is believed that xenon light sources actually emit energy from 220 to 1,200 nm, i.e. from the ultraviolet to the near infrared regions.

The desirable qualities of fiberoptic illumination are counteracted however by the high intensity of the light which can ignite certain non-heat resistant materials and cause them to melt. For instance several incidents of surgical theater fires ignited by fiberoptic illumination systems have been reported. There have been incidents where a fiberoptic cable was disconnected from an arthroscope and placed on a surgical drape while the xenon light source was still activated. The high-intensity output from such cables has caused cloth drapes to be ignited, causing smoldering fires with considerable smoke. Fortunately for some of the patients, elevated oxygen and nitrous oxide levels were not present (as they could have been near a patient's head during anesthesia) and the fires were generally extinguished before the patients suffered any burns. In other incidents however, disconnected fiberoptic cables actually ignited disposable nonwoven surgical paper drapes that had trapped pockets of oxygen, and, in at least one such incident a resulting flash fire severely burned a patient's leg. (*Health Devices*, Vol. 11, No. 11, 148–149, 1982.)

Many of the reports concerning fires caused by fiberoptic illumination systems reveal that the fires happened very quickly: within several seconds or a couple of minutes. These reports also reveal that holes of significant size were created in surgical drapes before the fire was extinguished. (M. A. Eggen et al, *Fiberoptic Illumination Systems Can Serve as a Source of Smoldering Fires*, Journal of Clinical Monitoring, vol. 10, no. 4, 244–246, (1995).)

One particularly dangerous misconception about the fiberoptic illumination systems is many users' belief that fiberoptic illumination systems supply "cold" light to the visual field. Actually, such light sources only reduce the amount of infrared radiation (that radiation usually associated with heat production) with respect to visible light. This is accomplished with special filters or lamp (dichroic) reflectors. Radiation in the visible and infrared wavelengths enters the fiberoptic cable and is transmitted through the cable and instruments. When the light leaves the endoscope tip, the level of infrared radiation has usually been reduced to a safe level through absorption by the optical fibers in the endoscope and substantial losses at the cable connections. However if the cable is not connected to the endoscope, the infrared output is not reduced sufficiently and can ignite some materials. This is especially true at high light source dial settings and with xenon arc lamps that have much higher output than conventional quartz-halogen (150-watt) lamps. (*Health Devices*, Vol. 11, No. 11, 148–149, 1982.).

The conditions of misuse usually involve the disconnecting of the fiberoptic cable from the endoscope and placing the distal end on a drape while the fiberoptic light source is activated. Radiation in the visible and infrared wavelengths from the light source passes through the fiberoptic cable and is transmitted to the instruments. If the instrument (such as an endoscope) is disconnected, the infrared output is not sufficiently reduced and can cause ignition or melting of the materials (i.e. surgical drape, or instrument pads) that the cable is resting on.

Instrument pads are used for the placement of surgical implements during surgery and are usually constructed of a type of polymer or plastic. Generally instrument pads are placed upon surgical drapes, or affixed thereto, so that surgeons may place instruments upon them, without fear of the instruments sliding off and falling to the ground. One particular disadvantage of using fiberoptic illumination systems in operating rooms is that because of the high intensity of heat generated, they may cause instrument pads or surgical drapes to melt or ignite. This can be very dangerous, for instance there is the potential for such instrument pads to melt and ooze into the surgical opening, thereby causing substantial damage. The side effects of such a mishap can be detrimental, if not fatal.

An additional concern is that advances in light source and fiberoptic technology may increase the radiation output of visible and infrared wavelengths at the end of the cable and at the distal tip of the endoscope. Higher outputs may increase the risk of even more fires in the operating room. Furthermore, increased use of television systems with video cameras connected to endoscopes, has caused many physicians to operate light sources at their maximum intensities and many believe that they need even greater light intensities. (*Health Devices,* Vol. 11, No. 11, 148–149, 1982.).

What is needed therefore is an improved instrument pad that can be used in the presence of fiberoptic illumination systems which is resistant to melting or catching on fire from the illumination system. Such an instrument pad should be versatile so that it can be used by itself or attached to a surgical drape. The instrument pad should also have features that allow it to hold surgical implements placed upon it, and should also comprise at least one storage pouch for use during surgery.

SUMMARY OF THE INVENTION

It has been found in accordance with the present invention that a sheet material composed of a film/foam laminate having a working surface that is resistant to heating by high intensity light may be employed as an improved fire resistant supporting surface for articles such as surgical instruments.

Features of the Invention

A feature of the invention is that the uppermost or working surface of the film/foam laminate sheet material of the invention is sufficiently reflective so as to not appreciably absorb infrared energy emitted by fiberoptic illumination systems commonly used during surgery.

Another feature of the invention is that the working surface is characterized by a high coefficient of friction.

Advantages of the Invention

An advantage of the film/foam laminate of the invention is that it resists melting and ignition by high intensity fiberoptic illumination. Accordingly, it is particularly suited as an instrument pad material, and for use in surgical drapes.

The laminate also provides a non-slip surface when the working surface has a high coefficient of friction. Accordingly, surgical instruments are retained and will not slip or slide-off an instrument pad made with the laminate.

The laminate according to the present invention is particularly useful as a versatile supporting surface for surgical instruments. Most importantly, the laminate does not appreciably absorb infrared energy emitted by fiberoptic illumination systems used in surgery. Accordingly, the laminate resists melting and ignition when used in the presence of fiberoptic illumination under surgical operating conditions, thereby making it possible for surgeons to perform medical procedures in well lighted environments without the potential complications of melting or fire associated with regular instrument pad materials. The technically significant qualities of the film/foam laminate prevent an instrument pad or surgical drape made therefrom from melting even when exposed to a high intensity of illumination. The laminate instrument pad of the present invention is either laid upon or attached to a surgical drape and may further incorporate fenestration sites as necessary.

Optionally, the instrument contacting surface of the laminate is textured to create a sufficient coefficient of friction so as to provide a non-slip surface to hold surgical instruments.

In one embodiment, the film/foam laminate comprises, a film layer, having a first film surface that is sufficiently reflective to fiberoptic illumination, particularly infrared energy associated with surgical fiberoptic illumination, to resist melting under surgical operating conditions, and a second film surface; and a foam layer having a first foam surface and a second foam surface, wherein said second foam surface is affixed to said second film surface to form a film/foam laminate.

The present invention provides an improved instrument pad that will resist melting in the presence of fiberoptic illumination. The present invention also provides an improved instrument pad that will resist melting in the presence of fiberoptic illumination and will also comprise a non-skid surface for supporting articles such as tools, surgical instruments and the like.

In addition, the present invention provides an improved instrument pad which will resist melting in the presence of fiberoptic illumination and which further comprises at least one pouch. Finally, the present invention provides an improved surgical drape comprising an improved instrument pad which resists melting from fiberoptic illumination and which optionally may contain at least one pouch.

These and other objects, features and advantages of the present invention will become apparent after a review of the following detailed description of the disclosed embodiments.

BRIEF DESCRIPTION OF THE FIGURES

FIG. 3 is an instrument pad 80 comprised of laminate 10.

FIG. 4 is an instrument pad 80 comprised of laminate 10, and further comprising an optional pouch 90 and an optional fenestration area 110 and fenestration site 120.

FIG. 5 is a surgical drape comprising an instrument pad 80 affixed to the fenestration area 110 of the working surface of the surgical drape 100 and pouch.

FIG. 6 is a surgical drape comprising an instrument pad 80 affixed to the fenestration area 110 of the working surface of the surgical drape 100 further showing a fenestration site 120 cut into the fenestration area 110 and pouch.

DETAILED DESCRIPTION

The present invention relates to an improved film/foam laminate material that resists melting by high intensity illumination, particularly fiberoptic illumination systems used in surgery, and especially xenon fiberoptic illumination. The laminate has utility as an improved instrument pad and when incorporated into a surgical drape. The film/foam laminate is characterized by a highly reflective upper working surface. The upper surface is sufficiently reflective to infrared energy emitted by fiberoptic illumination so as to withstand melting and ignition from high intensity surgical lighting as used under normal surgical operating conditions.

In the course of the invention described herein the following terms will be described and have the following applied meanings:

Film means a thin, flexible sheet or membranous coating or covering. Foam means a dispersion of gas in a liquid or solid. A laminate is a material containing two or more layers affixed together for example with resin, rubber, foam or adhesive or thermal bonding. The film/foam interface is the point at which the film and the foam come together and form the laminate. The fenestration site is an opening made in the laminate or in a surgical drape for allowing access to a surgical opening on a patient. The fenestration area is the area of the laminate or of a surgical drape wherein a clean fenestration site may be cut. A pouch is a bag like structure which is either an extension of the instrument pad laminate, or an attachment to the instrument pad laminate, and is useful for storage purposes during surgical procedures. The working surface is the upper surface of the laminate and instrument pad upon which instruments are placed during surgery. A high intensity light heat resistant pad is a pad specifically designed to absorb the energy produced by a high intensity light source. A nonwoven fabric means an assembly of fibers held together by mechanical interlocking in a random web or mat, by fusing of the fibers, or by bonding with a cementing medium such as starch, glue, casein, rubber, latex, a cellulose derivative or synthetic resin. Spunlace means material consisting of a blend of wood pulp and polyester fibers where the fibers are subjected to high-velocity water jets which entangle the fibers to achieve mechanical bonding. Spunbond/meltblown/spunbond (SMS) material is a fabric consisting of three thermally or adhesively bonded layers. Typically, the material is made of polypropylene for medical applications. Treatments are optionally applied to provide improved liquid penetration resistance. Spunbonded materials comprise continuous filaments that are formed by in-line melt spinning. Meltblown materials are similar to spunbonded materials, but the fibers generally are finer and may not be continuous.

The following detailed description of the claimed invention is in reference to FIGS. 1 through 5.

1. Film/Foam Laminate

Figure 1:
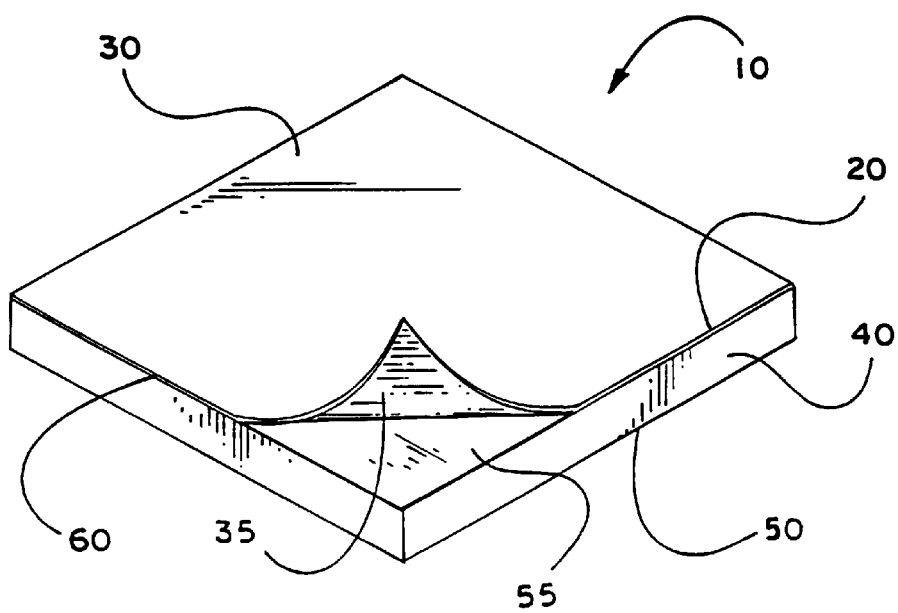
FIG. 1 is a film/foam laminate 10 comprising a film layer 20 having a first surface 30 and a second surface 35; and a foam layer 40 having a first surface 50 and a second surface 55. The film layer 20 and the foam layer 40 are joined together to form a film/foam interface 60.
Figure 2:
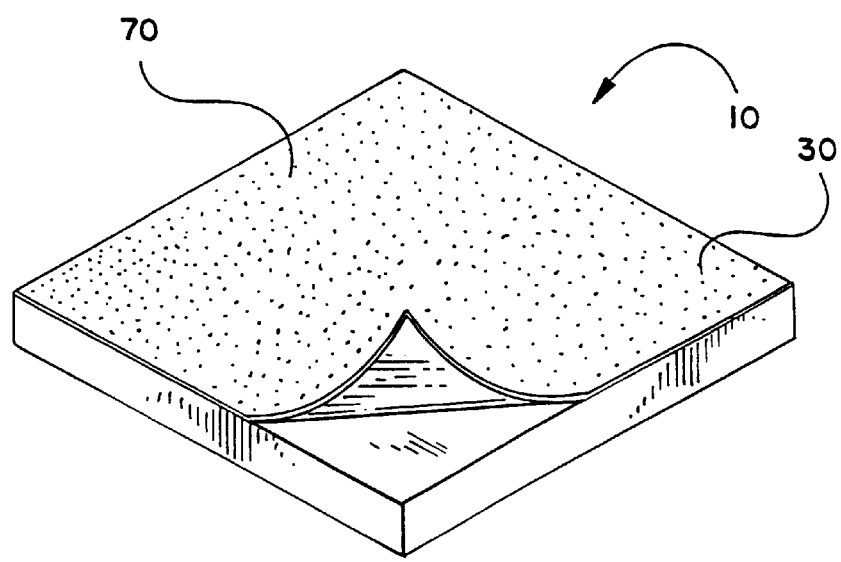
FIG. 2 is an alternative embodiment of the laminate 10 wherein the first film surface 30 is textured, for example having embossing thereon 70.

Referring now to FIG. 1, the claimed invention relates to a film/foam laminate 10 comprising, a film layer 20, having a first film surface 30 that is sufficiently reflective to fiberoptic illumination to resist melting, and a second film surface 35; and a foam layer 40 having a first foam surface 50 and a second foam surface 55, wherein said second foam surface 55 is affixed to said second film surface 35 to form a film/foam interface 60 and hence the film/foam laminate 10. The reflective first film surface 30 is used as the upper surface of the laminate in surgical application. Optionally, as shown in FIG. 2, the first film surface 70 is textured to create an increased coefficient of friction, so as to provide a non-slip surface for holding surgical instruments during surgery.

Desirably, the laminate comprises coextruded film comprising low density polyethylene and metallocene polyethylene that is approximately 1.0 mil in thickness, and having a white first film surface and a second film surface, wherein the second film surface is affixed to one surface of a closed cell foam having a first foam surface and a second foam surface, wherein the foam is approximately 31.25 mil in thickness.

2. Film

The first film surface 30 which serves as the top or upper surface of the instrument pad is reflective film. The function of the film is primarily to reflect infrared energy and to resist melting from high intensity light sources, and secondly to prevent surgical implements placed on the instrument pad from slipping or sliding off.

In order for film 20 to be effective at resisting melting from high intensity light sources, particularly fiberoptic illumination systems, the film upper surface 30 should be highly reflective, particularly to infrared energy. It is desirable that it be either transparent or white in color. Preferably the film should be able to reflect light energy in the range of approximately 220 mm to approximately 1,200 mm. By being highly reflective, the film absorbs very little heat and subsequently prevents the material from melting.

Desirably, the first film surface 30 is pigmented white to achieve a sufficient reflectivity to fiberoptic illumination. The thickness of the film is preferably in the range of approximately 0.9 to 1.1 millimeters, the density is approximately 0.915 and the preferred weight of the film/foam combination is approximately 1.18 osy. The film is further desirable because it is soft and drapeable. Examples of suitable film include those constructed from copolymers such as linear low density polyethylene (LLDPE) and ethylene vinyl acetate (EVA). These copolymers are soft, they enable thermal bonding and are therefore recommended constituents for the present invention.

The film desirably comprises co-extruded low density polyethylene (LDPE) and metallocene polyethylene. Coextruded film is generally preferred because it is stronger than films in which copolymers are not so well intermingled or connected. The thickness of the co-extruded film desirably ranges from approximately 0.9 to 1.1 millimeters, more desirably, from approximately 0.95 to 1.05 millimeters. A desirable film thickness is approximately 1.0 millimeters, when the film is co-extruded LDPE and metallocene polyethylene.

The film may optionally be formed to create a sufficiently high coefficient of friction on the first film surface 30 to provide a non-slip surface 70 for holding instruments during surgery. Film that has a high coefficient of friction is desirable for the present invention because it prevents objects from slipping off the surface. Since during medical procedures such as surgery, physicians must frequently lay down and then pick up various surgical tools, an instrument pad should be able to 'hold' or retain the items placed upon it. If the surface of the instrument pad is slippery or too smooth then objects placed upon it will not stay in place and could even fall off.

The laminate 10 of the present invention is suitable for use as an instrument pad. The coefficient of friction for the film should preferably be in the range of approximately 4.97 and 2.15 and suitable types of films may be constructed from a LDPE copolymer. One alternative method of constructing film having a suitable coefficient of friction is by embossing, for example by microflex embossing.

3. Foam

The base or bottom layer of the laminate is foam 40. The function of the foam is primarily as a substrate to support the reflective film and to retain surgical instruments when the laminate is used as an instrument pad. A particularly desirable foam is closed cell foam because it has a sealed surface; other suitable foams include urethane.

The foam layer of the instrument pad should preferably be approximately 28.0 to 32.0 millimeters in thickness. Desirably the foam layer of the laminate is closed cell foam that is approximately 31.25 millimeters in thickness.

4. Lamination

The second film surface 35 is affixed to the second foam surface 55 to ultimately form the film/foam laminate of the present invention. Where the film and the foam actually come together is designated the film/foam interface 60. The film and foam may be affixed by heat bonding, gluing with an adhesive, stitching, stapling or any other method for securing one layer to another.

5. Instrument Pads

Instrument pads made with the laminate of the invention can be constructed according to whatever dimensions are suitable for specific procedures. For example for minor uncomplicated surgeries, the instrument pad 80 could be of minimal size sufficient for holding a few number of instruments, as shown in FIG. 3. For more major and complicated surgeries the instrument pad 80 could be larger, having within it fenestration areas 110, fenestration sites 120, as well as pouches 90, as shown in FIG. 4. The instrument pad itself could be attached to a surgical drape 100 via stitching, bonding, gluing or other means well known in the art, as shown in FIGS. 5 and 6. Various other embodiments of such an instrument pad are possible ranging from combinations where the instrument pad is minimal and attached to just one side of the fenestration site, to where the instrument pad encompasses a large portion of the surgical drape and entirely surrounds the fenestration site.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

Experimental Data

EXAMPLE 1

Thin films of varying thicknesses from certain nonwoven materials were exposed to an unshielded fiber optic cable attached to a high energy xenon light source and analyzed for their energy absorbance in the ultra violet, visible and near infrared regions. Nonwoven materials alone or in combination with materials are commonly used for the construction of surgical gowns and drapes.

Five different types of materials were primarily tested: Kimberly Clark pigmented nonwovens, Baxter blue pigmented nonwovens, Baxter blue spunlace, and Clopay transparent and pigmented polyethylene films. In the first part of the experiment the absorbance spectra in the ultraviolet, visible, and near infrared regions, were obtained on films pressed from the materials. The ultraviolet, visible or near infrared spectra was not obtained on the spunlace sample since the fabric could not be pressed into a film. A summary of these absorption spectra is presented in Table 1.

TABLE 1

The Absorbance Peaks in the Ultraviolet, Visible and Near Infrared Regions

| Sample | UV 200–400 nm | Visible 400–750 nm | Near Infrared 750–2500 nm |
| --- | --- | --- | --- |
| White KC nonwoven | none | none | none |
| Blue KC nonwoven | none | none | 725 |
| Blue Clopay film | totally absorbs | mostly absorbs | 713 |
| White Clopay film | totally absorbs | mostly absorbs | 713 |
| Clear Clopay film | 205, 215 | none | none |
| Clopay foamed film | 205 | none | none |
| Scarlet H380 nonwoven | 225, 280 | 505, 557 | none |
| Blue 815 nonwoven | 225 | 670 | none |
| Beige EVOLUTION 4 nonwoven fabric | 225 | none | none |
| Dark Brown 358 nonwoven | 225, 325 | 450, 503, 555 | none |
| Light Brown 353 nonwoven | 225, 280 | 425 | none |
| Yellow 366 nonwoven | 225 | 400 | none |
| Grey Evolution Meltblown with CHIMASSORB 944 UV Stabilizer | 225 | 702 | none |
| Grey Evolution Meltblown with out CHIMASSORB 944 | none | 702 | none |

These results indicate that there is no simple correlation between the ultraviolet, visible, and near infrared absorbance spectra of a material and predicting whether that material will melt or scorch when exposed to an unshielded high energy fiber optic light. Other factors such as the ability of the material to reflect the energy and the ability of the excited material to dissipate the heat generated, therefore contributes to whether the material will melt or scorch.

In the second part of this experiment, the materials were placed on a sheet of white paper and subjected to an unshielded high energy fiber optic light source. In order to keep the end of the unshielded fiber optic cable at a constant height above the material, a 44×12.5 mm aluminum pan which had a circular hole punched in the bottom, was placed upside down over the material. The unshielded end of the fiber optic cable was placed against the hole in the pan while the other end of the fiber optic cable was attached to an Acuflex instrument fitted with a 6200° K, 300 watt automatic xenon light source and the results to that exposure were recorded. The Acuflex instrument was set on Filter C and the high intensity light switch was set at a low setting. The time taken to melt the material was recorded once the light switch was turned on. If the material showed no scorching or melting within one minute the test was stopped. The experiment was repeated with the materials which were not affected by the light, but this time the material was placed on black paper. A final test was carried out on the materials which did not melt. They were stained with red and blue inks and with blood. They were then placed on the white paper sheet and re-tested. The results of these initial experiments are summarized in Table 2.

TABLE 2

Interaction of Unshielded Fiber Optic Light from a High Energy Xenon Source on Colored Nonwovens, Clopay pads and Colored Spunlace

| Sample | Results |
| --- | --- |
| White paper | No scorching after 1 min |
| White nonwoven on white paper | No melting after 1 min |
| White nonwoven on black paper | No melting after 1 min |
| White nonwoven stained with inks or blood on white paper | Melts within ~5 seconds |
| Scarlet H380 nonwoven on white paper | Melts within ~5 seconds |
| Clear Clopay (film side up) on white paper | No melting after 1 rnin |
| Clear Clopay (foam side up) on white paper | No melting after 1 min |
| Clear Clopay (film side up) on black paper | Melts within ~5 seconds |
| White Clopay (white film side up) on white paper | No melting after 1 min |
| White Clopay (foam side up) on white paper | No melting after 1 min |
| White Clopay (film side up) on black paper | No melting after 1 min |
| Blue Clopay (film side up) on white paper | Melts within ~5 seconds |
| Blue Clopay (foam side up) on white paper | Melts within ~5 seconds but melting is less severe than seen on blue side |
| Clear Clopay stained with inks or blood on white paper | Melts within ~5 seconds |
| White Clopay stained with inks or blood on white paper | Clear Clopay stained with inks or blood on white paper |
| Blue spun lace (paper side up) on white paper | Slightly scorched after ~5 seconds |
| Blue spun lace (polyester side up) on white paper | Very slightly scorched after ~5 seconds |
| Dark brown H380 nonwoven on white paper | Melts within ~5 seconds |
| Light brown H353 nonwoven on white paper | Melts within ~5 seconds |
| Blue 815 nonwoven on white paper | Melts between 5 & 10 seconds |
| Yellow 366 nonwoven on white paper | No melting after 1 minute |
| Evolution 4 Beige nonwoven on white paper | Melts between 5 & 10 seconds |
| Grey Evolution nonwoven on white paper | Melts within ~5 seconds |
| K-C Blue nonwoven drape on white paper | Melts within ~5 seconds |

The above results indicate that an unshielded high energy fiber optic light source, such as one which is not attached to an endoscope, will usually melt most colored nonwovens and colored Clopay pads, and will scorch colored spunlace materials. It appears that most colored nonwovens, colored spunlaces and colored Clopay films, absorb energy from the unshielded fiber optic source resulting in the melting or scorching of the material. The exceptions appear to be white and yellow nonwovens and white or clear Clopay pads. The shiny transparent Clopay film either transmits or reflects sufficient energy so that the film does not melt. The white titanium dioxide filled Clopay reflects energy.

EXAMPLE 2

Thin films of varying thicknesses were pressed from the materials as in Example 1 (with the exception of the spunlace which could not be pressed into film form). The thin films were then scanned on a Beckman® 35 spectrophotometer in the ultraviolet and visible regions (200–360 nm, and 360–700 nm). The films were rescanned in the near infrared region (700–1,136 nm) on a Nicolet 740 Fourier Transform Infrared Spectrophotometer using a quartz halogen near infrared-visible source, a quartz beam splitter and a silicon detector.

It is important to stress that halogen quartz sources have much less energy output than xenon arc sources, and the Nicolet 740 spectrophotometer uses a quartz halogen lamp for their near infrared source. Therefore, light generated by xenon sources (having a greater energy output) will to a greater degree be absorbed by the above materials which were exposed to energy generated by a quartzhalide source in these experiments. Results of this experiment are summarized in Table 3.

TABLE 3

| Sample | Absorbancy UV 200–360 | Absorbancy Vis 360–700 | Absorbancy NIR 700–1136 | Effect to Exposure of unshielded fiber optic cable/ Xenon light |
|---|---|---|---|---|
| White K-C nonwoven | no | no | no | none |
| Blue K-C nonwoven | no | no | yes | melts |
| Blue Baxter nonwoven | no | no | yes | N/A |
| K-C Scarlet H380 nonwoven | yes | yes | no | melts |
| K-C Blue 815 nonwoven | yes | yes | no | melts |
| K-C Beige E4 nonwoven | yes | no | no | melts |
| K-C Brown 358 nonwoven | yes | yes | no | melts |
| K-C Brown 353 nonwoven | yes | yes | no | melts |
| K-C Yellow 366 nonwoven | yes | yes | no | none |
| K-C Gray Evolution meltblown | yes | yes | no | melts |
| Baxter Blue Spunlace | N/A | N/A | N/A | scorches |
| Blue PE film (Clopay) | yes | yes | yes | none |
| Transparent PE film (Clopay) | yes | no | no | none |

These results indicate that most colored materials will melt or scorch upon exposure to unshielded fiber optic cable/xenon light. The exceptions appear to be white and yellow nonwoven materials, and transparent and blue polypropylene Clopay film.

EXAMPLE 3

The films were pressed of varying thickness because absorbancies were not detected in the near infrared region on the Nicolet 740 spectrometer when the thinner films which had been scanned on the Beckman UV-Vis spectrophotometer were used. In general 25 micron thick films were scanned in the UV-Vis region. In the near infrared the film thickness was either 65, 100 or 500 microns. Absorbancy versus film thickness for some of the samples are summarized in Table 4.

TABLE 4

| Film | Thickness (microns) | Light | Absorption |
|---|---|---|---|
| KC White Non Woven | 25 | Visible | No |
| KC Blue Non Woven | 25 | Visible | No |
| KC White Non Woven | 25 | Ultraviolet | No |
| KC Blue Non Woven | 25 | Ultraviolet | No |
| Baxter (Blue) | 25 | Visible | No |
| Baxter (Blue) | 25 | Visible | No |
| KC White Non Woven | 65 | Near Infrared | No |
| KC White Non Woven | 100 | Near Infrared | No |
| KC White Non Woven | 500 | Near Infrared | No |
| Baxter (Blue) | 65 | Near Infrared | No |
| Baxter (Blue) | 100 | Near Infrared | Yes |
| Baxter (Blue) | 500 | Near Infrared | Yes |
| KC Blue Non Woven | 65 | Near Infrared | Yes |
| KC Blue Non Woven | 100 | Near Infrared | Yes |
| KC Blue Non Woven | >500 | Near Infrared | Yes |

The above experiments demonstrate that generally the thicker the film, the greater the absorbance. Importantly these results also demonstrate that any non-white pigmented material will melt upon exposure to high intensity light.

While the invention is characterized by the above descriptions and embodiments, one skilled in the art will understand that many obvious variations are possible. All such variations of the invention are intended to fall within the scope of the appended claims.

We claim:

1. A film/foam laminate comprising;
    a film layer, having a first film surface that is sufficiently reflective to fiber optic illumination to resist melting, and a second film surface; and
    a foam layer having a foam surface;
    wherein said foam surface is affixed to said second film surface to form a film/foam laminate.

2. The laminate of claim 1 wherein the film is co-extruded low density polyethylene (LDPE) and metallocene polyethylene.

3. The laminate of claim 1 wherein the film is co-extruded linear low density polyethylene (LLDPE) and ethylene vinyl acetate (EVA).

4. The laminate of claim 1 wherein the foam is closed cell foam.

5. The laminate of claim 1 wherein the first film surface is embossed to provide a sufficient coefficient of friction to hold instruments placed on the instrument pad.

6. The laminate of claim 5 wherein the coefficient of friction ranges from 4.97 to 2.15.

7. The laminate of claim 1 wherein the first film surface is white in color.

8. The laminate of claim 1 wherein the first film surface is transparent.

9. The laminate of claim 2 wherein the thickness of the film ranges from approximately 0.9 mm to 1.1 mm.

10. The laminate of claim 2 wherein the thickness of the film ranges from approximately 0.95 mm to 1.05 mm.

11. The laminate of claim 2 wherein the thickness of the film is 1.0 mm.

12. The laminate of claim 1 wherein the foam is closed cell foam the thickness of which is in the range of approximately 28 mm to 32 mm.

13. The laminate of claim 1 wherein the coextruded film comprises low density polyethylene and metallocene polyethylene, and is approximately 1.0 mil in thickness, and wherein the foam is closed cell foam that is approximately 31.25 mil in thickness.

14. A surgical drape comprising the laminate of claim 1 attached to at least one edge of the fenestration area of a surgical drape.

15. The surgical drape of claim 1 wherein the laminate is formed so as to provide a pouch.

* * * * *